United States Patent [19]

Vadher

[11] Patent Number: 5,024,256

[45] Date of Patent: Jun. 18, 1991

[54] VIAL CONSTRUCTION AND METHOD

[76] Inventor: Dinesh L. Vadher, 48 Rte. 25A-Suite 303, Smithtown, N.Y. 11787

[21] Appl. No.: 502,711

[22] Filed: Apr. 2, 1990

[51] Int. Cl.[5] .......................... B65B 1/04; A61B 19/00

[52] U.S. Cl. ...................................... 141/329; 140/27; 604/415

[58] Field of Search ............... 141/329, 330, 319, 320, 141/321, 25, 26, 27; 604/905, 415, 411, 414, 407, 403, 244

[56] References Cited

U.S. PATENT DOCUMENTS

| | | | |
|---|---|---|---|
| 853,097 | 5/1906 | Linker | 215/313 |
| 1,449,768 | 3/1923 | Mailman | 215/313 |
| 2,123,906 | 7/1938 | Masbach et al. | 215/313 |
| 2,533,915 | 12/1950 | Brooks | 215/313 |
| 2,667,986 | 2/1954 | Perelson | 141/329 |
| 3,005,455 | 10/1961 | Poitras et al. | 604/415 |
| 3,603,471 | 9/1971 | Harris et al. | 215/37 |
| 4,564,054 | 1/1986 | Gustavsson | 604/411 |
| 4,576,211 | 3/1986 | Valentini | 141/229 |

*Primary Examiner*—Henry J. Recla
*Assistant Examiner*—David J. Walczak
*Attorney, Agent, or Firm*—Leonard Belkin

[57] ABSTRACT

A vial containing liquid contents constructed so as to permit transfer of its contents to a syringe without the use of a needle with the syringe. One embodiment employs rotation of a cap to align openings avoiding the use of a needle. In another embodiment, there is provided mounted within apparatus located on the mouth of the vial a needle which is built in to the apparatus. The syringe engages the needle which is then depressed to puncture the cork sealing the vial, the vial is then inverted, and the contents drained into the syringe. The needle is withdrawn thereby resealing the contents of the vial, and the needle remains with the vial.

1 Claim, 2 Drawing Sheets

FIG. 1
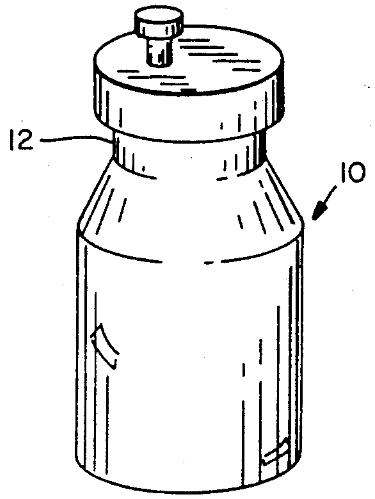
FIG. 2
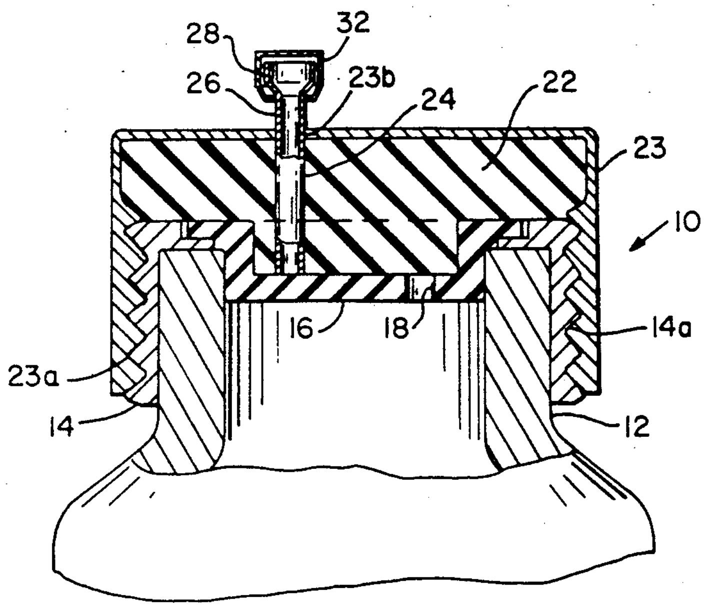
FIG. 1a
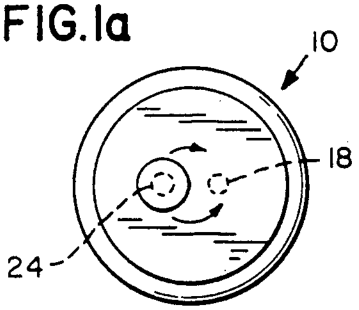
FIG. 3
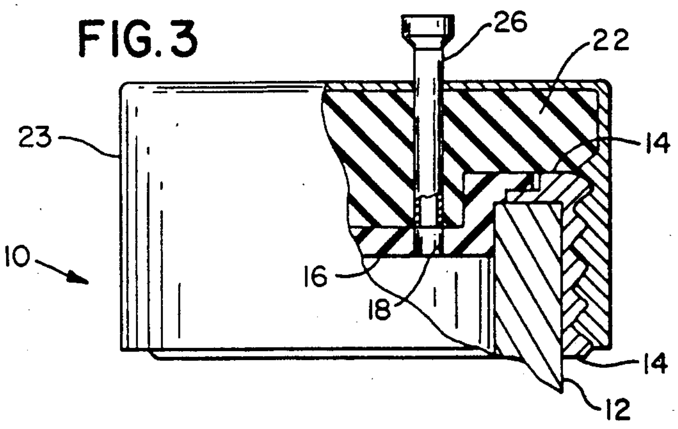
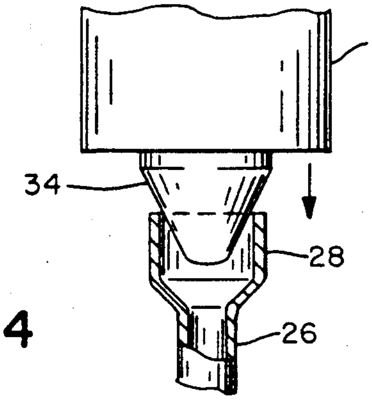
FIG. 4
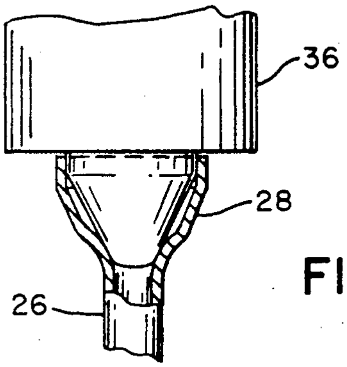
FIG. 4a FIG. 5
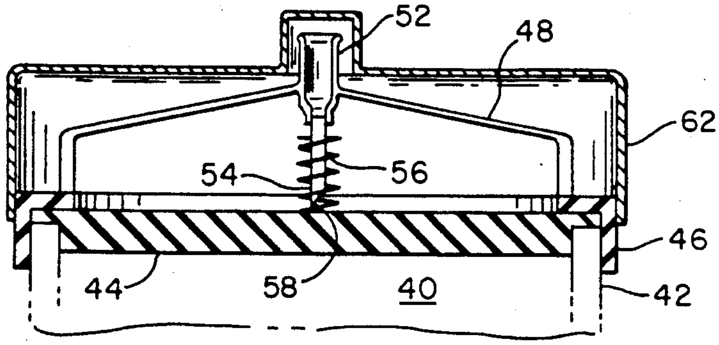
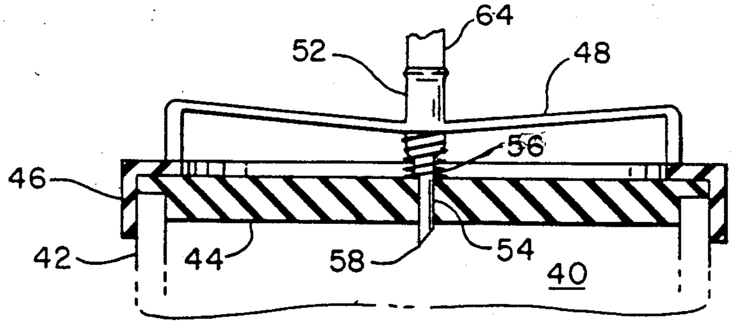
FIG. 7
FIG. 6
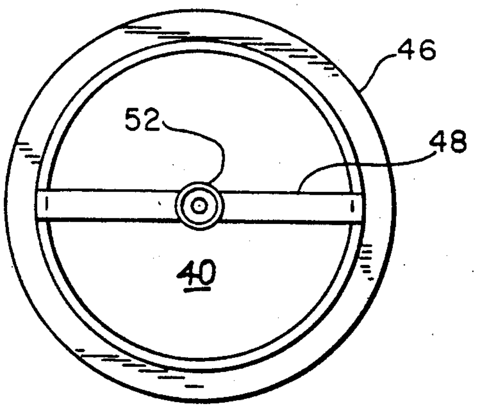
FIG. 8
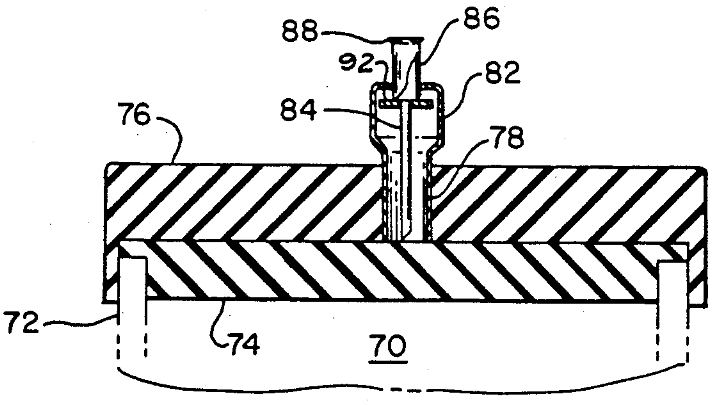

VIAL CONSTRUCTION AND METHOD

BACKGROUND OF THE INVENTION

The present invention relates to apparatus for facilitating the transfer of the contents of a vial to a syringe without the need to handle a needle.

The handling of needles by medical workers has become a troublesome problem due to the risk of accidental puncture which happens all too frequently in the hurried atmosphere of a hospital, especially in emergency rooms.

Because of the existence of communicable diseases which can be transferred by body fluids such as blood, especially in a hospital environment, there is growing concern over the accidental punctures of medical care workers by needles.

A number of United States Patents show arrangements for capping and removing the contents of a container.

U.S. Pat. Nos. 853,097, 1,449,768, 2,123,906, and 3,005,455 show a variety of arrangements for aligning openings in container covers to permit the removal of the contents of the container.

U.S. Pat. No. 2,533,915 adds a yieldable locking means while U.S. Pat. No. 3,603,471 has provision for the insertion of a needle which is then withdrawn.

None of the preceding patents discloses or teaches the present invention.

SUMMARY OF THE INVENTION

This invention reduces the risk of accidental needle penetration of a medical worker by eliminating the use of a separate needle requiring handling in the transfer of liquid medication from a vial to a syringe.

According to one embodiment of this invention, no needle is involved in the transfer of the contents of a vial to a syringe. In this arrangement, the closure consists of a stationary member with an opening and a rotatable cover member with an opening in which is mounted a tube having a luer or other connector for engaging the syringe. To remove the contents of the vial, the rotatable cover is turned to align the openings, the syringe is attached to the connector, and the vial is turned over to facilitate transfer of the contents. The procedure is reversed to reseal the vial for later use.

In another embodiment of the present invention there is provided a vial with a cap which incorporates as a permanent part of the cap a fully enclosed needle to penetrate the cork when the need arises to make the transfer. The needle is provided with a suitable luer or other connecter for engagement with the syringe to receive the contents of the vial. As is understood in the art, the cork is made from material which is self-sealing when the needle is retracted. The needle remains as part of the cap assembly and can be reused the next time medication is to be removed.

It is thus a principal object of this invention to provide apparatus and method for the transfer of the contents of a vial to a syringe without the use of an exposed needle.

Other objects and advantages of this invention will hereinafter become obvious from the following description of preferred embodiments of this invention.

BRIEF DESCRIPTION OF THE DRAWINGS

FIG. 1 is a perspective view of a vial embodying the principles of this invention.

FIG. 1*a* is a top view of the vial shown in FIG. 1.

FIG. 2 is an elevation view partially cut away and in section showing the upper portion of the vial illustrated in FIG. 1, with the vial in the sealed condition.

FIG. 3 is a detail in partial section of a portion of the top of the vial shown in FIG. 2 ready for removal of the contents of the vial.

FIGS. 4 and 4*a* illustrate how a syringe is mated with the vial to withdraw the contents.

FIG. 5 is an elevation view in section of the top part of a vial showing another embodiment of this invention.

FIG. 6 is a top view of the vial shown in FIG. 5 with the cover removed.

FIG. 7 is a view similar to that of FIG. 5 with the needle positioned to withdraw contents of the vial.

FIG. 8 is an elevation view in section of the top part of a vial showing still another embodiment of this invention.

DETAILED DESCRIPTION OF THE PREFERRED EMBODIMENTS

Referring to FIGS. 1–3, vial 10 is provided with a neck 12 open on the top on which is mounted a collar 14 supporting a closure 16 extending into neck 12 forming a pocket and having a circular opening 18. This construction insures a proper sealing of the contents within vial 10.

A rotatable cap 22 with a passageway 24 is mounted on on top of neck 12 across collar 14 and closure 16 filling the pocket formed by closure 16 above opening 18. This arrangement provides improved sealing while permitting cap 22 to be rotated as will be described below.

A snap-on cover 23 encloses the whole assembly just described engaging through ridges 23*a* similar ridges 14*a* on collar 14. Cover 23 is rotatable with respect to collar 14 which is fixed, and is keyed to rotate along with cap 22. That is, when cover 23 is turned, cap 22 will turn with it. Cover 23 is provided with an opening 23*b* which corresponds with and is aligned with passageway 24 in cap 22.

An outlet tube 26 with a suitable fitting 28 for engagement with a syringe, as will be described later, is mounted in cap 22 extending through opening 23*b* and passageway 24 with fitting 28 exposed above cover 23 as illustrated. Tube 26 effectively keys cover 23 and cap 22 together although additional means such as an adhesive may be employed. A snap-on dust cover 32 is shown covering fitting 28 and would be removed when contents of vial 10 are to be removed. Passageway 24 is located on the same circular arc as opening 18 as seen in FIG. 1*a*.

When it is desired to tap the contents of vial 10, cover 23 along with cap 22 are rotated until tube 26 is aligned with opening 18 in closure 16 as seen in FIG. 3. As seen in FIG. 4, fitting 34 of syringe 36 is inserted into fitting 28 of tube 26 until the connection by friction is firm as seen in FIG. 4*a*. Then vial 10 is turned over to draw out the contents of vial 10 in the usual manner, manipulating the plunger (not shown) as known in the art within syringe 36 for this purpose. Vial may be collapsible to prevent air from replacing the removed contents.

When the desired amount of the liquid contents of vial 10 is removed by syringe 36, vial 10 would by turned right side up and syringe 36 removed. Then cover 23 and cap 22 would be rotated to reseal the vial as seen in FIG. 2.

One of the advantages of the arrangement just described is that vial 10 and syringe 36 can be moved or handled without an exposed needle, and in the event the contents of the syringe are utilized without a needle, such as being attached or connected to an IV, then there is no needle to be disposed of at all.

Under circumstances where it is desired to employ a vial not having a cap with an opening prepared in advance, the embodiment of this invention shown in FIGS. 5, 6, and 7 may be employed.

There it will be seen that vial 40 has mounted on its neck 42 a cork 44 which seals the top opening into vial 40. Cork 44 is made of an elastic material such as cork or rubber so that when penetrated by a needle which is then removed the opening made by the needle is resealed as is understood in the art. Mounted on top of cork 44 and around the top edge of neck 42 is an annular ring 46 which keeps cork 44 in place and supports a member 48 extending along a diameter of the opening formed by ring 46 as seen more particularly in FIG. 6. The center of member 48 spanning ring 46 carries a hollow tube 52 from which extends downwardly a needle 54 surrounded by a spring 56. Needle 54 is provided with a sharp tip 58 at the bottom thereof. The top of tube 52 is provided with a luer or other type of connector for engaging the syringe.

As seen in FIG. 5, a dust cover 62 is frictionally attached to cover ring 46 when the vial is not in use. Cover 62 is removed when it is desired to remove contents from within vial 40.

To remove liquid from within vial 40, after cover 62 is removed, adaptor 64 of a syringe is inserted into the opening of tube 52 designed for this purpose and pressed downwardly compressing spring 56 and causing needle 54 to penetrate cork 44 as is understood in the art. Vial 40 and its attached syringe will then be upended to permit the syringe to be manipulated to remove the desired amount of contents from vial 40.

Vial 40 then will be turned right side up and the syringe removed so that spring 56 will retract needle 54, and cover 62 put in place. As previously explained, the hole made by needle 54 will reseal itself once the needle is removed.

If it is desired to dispense with the use of a spring, the embodiment shown in FIG. 8 may be employed. In this arrangement, there is shown vial 70 with neck 72 on which is mounted a cork 74 on top of which is secured a cap 76 with an opening 78. Mounted in opening 78 is a needle housing 82 containing a needle 84 connected at the top to a hollow member or housing 86 having a suitable adaptor or fitting 88 extending out of hollow member 86 for engaging a syringe. While not shown, it is understood there would be provided a dust cover which would be removed prior to withdrawing contents of vial 70. A flange 92 mounted between needle 84 and hollow member 86 limits movement of needle 84 in both directions.

To employ the arrangement shown in FIG. 8, the syringe (not shown) would be connected to adaptor 88 and pressed down so that needle 84 would penetrate completely through cork 74. The liquid contents would be removed in the manner previously described, that is, by upending vial 70. Vial 70 is resealed by turning vial 70 right side up and manually retracting needle 84 from cork 77 permitting the opening to become sealed, as previously described. In this arrangement, it may be desirable to provide a threaded coupling between the syringe and hollow member 86 so that the syringe could be utilized to raise needle 84. For this purpose, member 86 could be threaded on the outside and the syringe would be provided with matching threads.

In all of the embodiments of this invention described, there is no needle which has to be separately handled or exposed involved in the removal of liquid medication from a vial, thus reducing the risk to medical workers of puncture.

It will be noted that all of the arrangements are simple in construction, easy to use, and are safely disposable with any needles present which are thoroughly enclosed.

While only certain preferred embodiments of this invention have been described it is understood that many variations are possible without departing from the principles of this invention as defined in the claims which follow.

What is claimed is:

1. A self-sealing closure for an open mouth vial comprising:

a. a vial assembly including a vial with an open mouth defining a rim and having closure means of penetratable, self-sealing material mounted on, extending into and closing said mouth for sealing the contents of said vial;

b. collar means forming an annular ring mounted on the rim of said open mouth for enclosing the edge of and supporting said closure means;

c. means mounted on said collar means above said closure means outside of the mouth of said vial for supporting a needle having a pointed end directed toward said closure means and permitting axial movement of said needle comprising a vertically extending hollow tube having integral therewith a narrow member spanning and joining said annular ring forming a resilient structure permitting vertical movement of said hollow tube, said needle joined at the top thereof to and communicating with the bottom of said hollow tube, said needle having a pointed bottom facing said closure means;

d. means for biasing said needle means away from said closure means comprising a spring wrapped around said needle extending between the top of said closure means and the bottom of said hollow tube;

e. adaptor means mounted on the top of said hollow tube for attachment to and permitting communication with syringe means for receiving the contents of said vial and to depress said needle overcoming said bias to penetrate said closure means to gain access to the contents of said vial through said needle, the removal of said syringe means permitting said needle to retract from said closure means thereby resealing the contents of said vial, said closure means, collar means and mounted means including said needle forming an integral, non-removable part of said vial assembly; and f. dust cover means covering the top of said vial assembly including said collar means, mounted means, biasing means, and said adaptor means forming a vial assembly containing its own means for removing its contents.

* * * * *